(12) United States Patent
Hahn et al.

(10) Patent No.: US 10,408,781 B2
(45) Date of Patent: Sep. 10, 2019

(54) REFERENCE ELECTRODE INSERT FOR AN ELECTROCHEMICAL TEST CELL

(71) Applicant: EL-CELL GmbH, Hamburg (DE)

(72) Inventors: Michael Hahn, Hamburg (DE); Matthias Hahn, Barsinghausen/Kirchdorf (DE)

(73) Assignee: EL-CELL GMBH, Hamburg (DE)

( * ) Notice: Subject to any disclaimer, the term of this patent is extended or adjusted under 35 U.S.C. 154(b) by 276 days.

(21) Appl. No.: 15/120,713

(22) PCT Filed: Feb. 21, 2014

(86) PCT No.: PCT/EP2014/053409
§ 371 (c)(1),
(2) Date: Aug. 22, 2016

(87) PCT Pub. No.: WO2015/124198
PCT Pub. Date: Aug. 27, 2015

(65) Prior Publication Data
US 2017/0016844 A1 Jan. 19, 2017

(51) Int. Cl.
*H01M 10/0525* (2010.01)
*G01N 27/30* (2006.01)
*G01N 27/403* (2006.01)
*H01M 10/42* (2006.01)
*H01M 10/48* (2006.01)

(52) U.S. Cl.
CPC ......... *G01N 27/301* (2013.01); *G01N 27/403* (2013.01); *H01M 10/0525* (2013.01); *H01M 10/4285* (2013.01); *H01M 10/482* (2013.01)

(58) Field of Classification Search
CPC .......... H01M 10/052; H01M 10/0525; H01M 10/44; H01M 10/46
See application file for complete search history.

(56) References Cited

U.S. PATENT DOCUMENTS

| 3,325,378 A | 6/1967 | Greene et al. |
| 4,314,896 A | 2/1982 | Binder et al. |
| 2008/0083620 A1* | 4/2008 | Hirshberg .......... G01N 27/4035 204/416 |

FOREIGN PATENT DOCUMENTS

GB 2 095 409 A 9/1982

OTHER PUBLICATIONS

El-Cell, "ECC-Stand Docking station for test cells ECC-STD, ECC-Ref, ECC-RingRef and ECC-Aqu User Manual." *El-Cell electrochemical test equipment*, Feb. 2014, http://el-cell.com/wp-contect/uploads/manuals/ECC_STAND_manual.pdf.
(Continued)

*Primary Examiner* — Olantunji A Godo
(74) *Attorney, Agent, or Firm* — Saliwanchik, Lloyd & Eisenschenk (57) ABSTRACT

A reference electrode insert (14) for an electrochemical test cell (10), in particular for testing lithium ion cells, comprising a reference electrode (46) and a sleeve (15) for holding the reference electrode (46), characterized in that the sleeve (15) and the annular reference electrode (46) form a structural unit, the reference electrode (46) being secured firmly and captively in the sleeve in an encapsulated manner.

20 Claims, 5 Drawing Sheets

(56) References Cited

OTHER PUBLICATIONS

El-Cell, "Electrochemical Test Cell ECC-Ref User Manual." *El-Cell electrochemical test equipment*, Jan. 2014, http://el-cell.com/wp-content/uploads/manuals/ECC_REF_manual.pdf.
El-Cell, "Products 2014 Instrumentation for battery research." *El-Cell electrochemical test equipment*, Sep. 2014, http://el-cell.com/wp-content/uploads/EL-CELL_ProductFlyer_September2014.pdf.

* cited by examiner

REFERENCE ELECTRODE INSERT FOR AN ELECTROCHEMICAL TEST CELL

CROSS REFERENCE TO A RELATED APPLICATION

This application is a National Stage Application of International Application Number PCT/EP2014/053409, filed Feb. 21, 2014; which is incorporated herein by reference in its entirety.

The invention relates to a reference electrode insert for an electrochemical test cell, in particular for testing lithium ion cells, comprising a reference electrode and a sleeve for holding the reference electrode.

In researching and developing electrochemical storage cells, for example lithium ion storage batteries, electrochemical test cells are used to characterise the battery materials. In a three-electrode test cell, a defined pressure is applied to an electrode arrangement having a working electrode, counter electrode and reference electrode in mutual electrolytic contact. Via external terminals, which are conductively connected to the electrodes, electrical characteristic curves for characterising the used battery materials are obtained, for example current/voltage characteristic curves, constant current cycles and impedance spectra.

A conventional electrochemical test cell from the applicant, known by the name ECC-Ref, comprises an electrode arrangement having a working electrode, a counter electrode and an electrolyte-impregnated separator layer, a sleeve for holding the electrode arrangement, a steel cylinder which can be inserted into the sleeve from one side as a first accumulator, and a cup-shaped high-grade steel base enclosing the sleeve as a second accumulator. In the sleeve, a through-hole is provided, into which the user initially presses the reference material, for example lithium metal, usually using a special tool. The reference material is to reach as precisely as possible as far as the inner face of the sleeve. Subsequently, the sleeve prepared with reference material is inserted into the cup-shaped high-grade steel base from above, and a plurality of further steps are carried out. The preparation of the sleeve with the reference material is time-consuming and heavily dependent on the skill of the user.

A conventional test cell station from the applicant for receiving up to five test cells is known by the name ECC-Stand. The test cell station is connected via two cables to a terminal box, which has connection sockets for connection to an electronic control and signal processing device (battery tester or multi-channel potentiostat). An internal USB data logger may optionally be provided in the terminal box.

The object of the invention is to reduce the complexity of the construction of an electrochemical reference test cell for the user and to improve the reproducibility of battery test results.

The invention achieves the object by means of the features of the independent claims. Accordingly, the sleeve and the reference electrode form a structural unit, the reference electrode being secured firmly and captively in the sleeve in an encapsulated manner. The reference material can thus already be installed in the sleeve by the manufacturer, and the structural unit consisting of the sleeve and reference electrode can be supplied to the user as a disposable part. According to the invention, the quality of the reference electrode is no longer dependent on the skill of the user, but can instead be ensured by the manufacturer in a precise and reproducible manner. The encapsulation according to the invention of the reference electrode in the sleeve prevents the reference material from falling out or accidentally being mishandled by the user.

As a result of the annular reference electrode according to the invention, long-term test measurements, for example over 1000 hours, are reliably possible. For the punctiform connection known from the prior art of the reference electrode to the working/counter electrode, under unfavourable circumstances, gas bubble formation could cause the reference contact to be interrupted after a certain amount of time, and so reliable measurements were only possible for a much shorter period.

Preferably, the sleeve comprises a first sleeve part, a second sleeve part, and connection means which act between the sleeve parts and by means of which the sleeve parts are captively interconnected. This makes possible simple and rapid manufacture of the reference electrode insert according to the invention by the manufacturer. Snap-in or clip connection means are particularly preferable, but a screw or adhesive connection is also possible.

The sleeve advantageously consists of a battery-grade material, in particular a thermoplastic battery-grade plastics material, for example polypropylene PP or high-density polyethylene HDPE having a density of between 0.94 and 0.97 g/cm$^3$. This is advantageous over conventional test cells consisting of components which are usually manufactured by machining, this being impossible or difficult to carry out for battery-grade materials. By contrast, a battery-grade plastics material, in particular PP or HDPE, can be processed in a simple manner by injection moulding. Battery-grade materials are generally those materials which are also used in commercial batteries.

Preferably, the reference electrode comprises an in particular metal support ring, in which at least one recess for receiving the reference material is provided. Preferably, the support ring comprises a plurality of recesses distributed over the circumference thereof for receiving the reference material. However, the recess may also for example be an annular groove.

Preferably, the reference electrode arrangement comprises a contact ring, in particular made of metal, which is in electrical contact with the support ring. On the one hand, the contact ring serves to establish the electrical contact of the reference material with an external electrical reference terminal of the test cell, and can be formed adapted to this function. For example, the contact ring may be thinner than the support ring. The contact ring may advantageously have an angled tab as a spring contact tongue for electrical connection to an external electrical terminal. On the other hand, the contact ring advantageously reduces the impedance of the reference electrode (shunt effect at high measurement frequencies).

In a preferred embodiment, the membrane is formed by an electrolyte-impregnated separator, which is arranged between the working electrode and the counter electrode and advantageously consists of a plastics film, in particular a polyolefin film, or a fibre mat, in particular a glass fibre mat. The separator prevents an electrical short-circuit between the working electrode and counter electrode, and in this embodiment also serves as a "wick" for the reference electrode, ensuring the required electrolyte contact between all three electrodes. In this embodiment, the separator is advantageously assembled by the manufacturer, and is part of the reference electrode insert that is secured firmly and captively in the sleeve. Preferably, the separator is clamped to the sleeve using the support ring.

In an alternative embodiment, the membrane may be annular. In this case, the annular membrane installed by the manufacturer takes on merely the function of the "wick", so as to produce the electrolyte contact with the reference material. In this case, the user can use any desired separator. This may for example be advantageous if the user wishes to use a thicker separator for example consisting of glass fibres.

An electrochemical test cell according to the invention comprises a first accumulator, a second accumulator and an electrode arrangement, arranged between the first and the second accumulator, comprising a working electrode, a counter electrode and an above-described reference electrode insert. The accumulators advantageously consist of a battery-grade metal, in particular high-grade steel (for example 1.4404), copper (for example E-Cu58, material No. 2.0060) or aluminium (for example AL 99.85 or EN AW-1085). The accumulators may each be configured as a reusable part (in particular in the case of high-grade steel) or as a disposable part (in particular in the case of Cu, Al). The housing of the test cell encloses the inner cell (accumulators and electrode arrangement) and seals them off hermetically from environmental influences by means of appropriate seals.

Further advantageous aspects of the invention relate to a test cell station comprising a housing and at least one, preferably a plurality of receptacles provided in the housing for at least one, preferably a corresponding plurality of electrochemical test cells. A circuit board, arranged inside the housing, and the test cell may be electrically connected advantageously by means of dual-action spring contact pins, which are designed for resilient contact with contacts on the test cell at one end and for direct, resilient contact with contacts on the circuit board at the other end. Conventional cable connections thus become superfluous at this point.

Advantageously, the test cell on a contact face contacting a test cell station may comprise a conductive contact element for presence detection. The presence of a test cell in a receptacle of the test cell station can be determined in a simple manner if two contacts, which are short-circuited by the contact element of the test cell, are provided in the receptacle.

Preferably, a data logger for recording charge characteristics is integrated into the housing of the test cell station. A separate terminal box known from the prior art and the corresponding connection cables are thus unnecessary.

The test cell according to the invention is advantageously provided for researching and developing electrochemical storage cells, in particular electrochemical secondary cells or secondary batteries, electrochemical primary cells and electrochemical capacitors, for example double-layer capacitors.

In the following, the invention is explained on the basis of preferred embodiments with reference to the accompanying drawings, in which.

Figure 1:
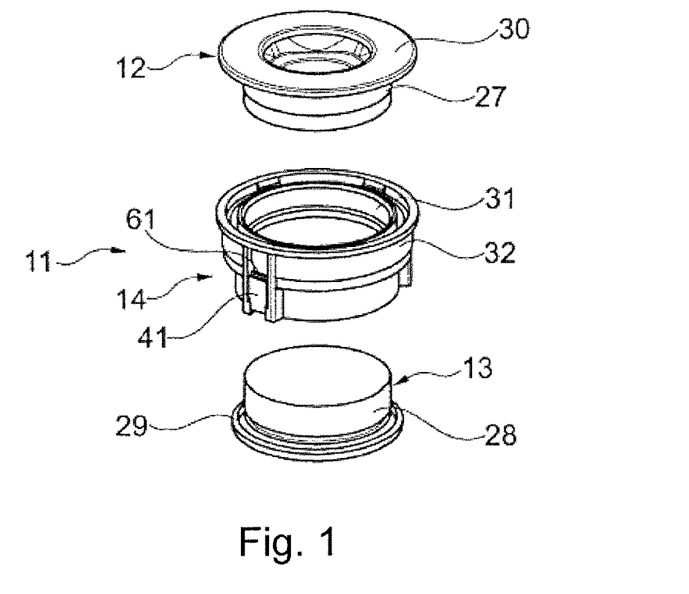
FIG. 1 is an exploded view of an inner cell for an electrochemical test cell.
Figure 2:
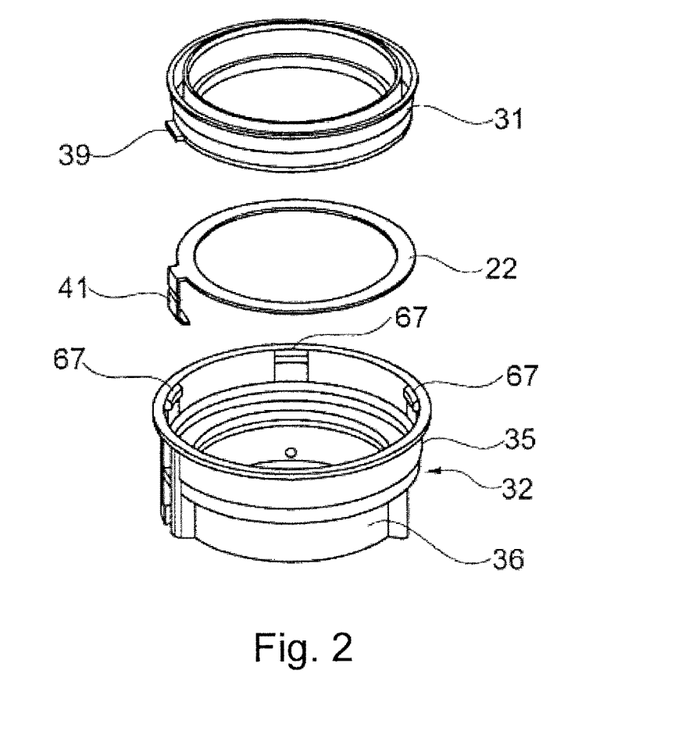
FIG. 2 is an exploded view of a reference electrode insert according to the invention.
Figure 7:
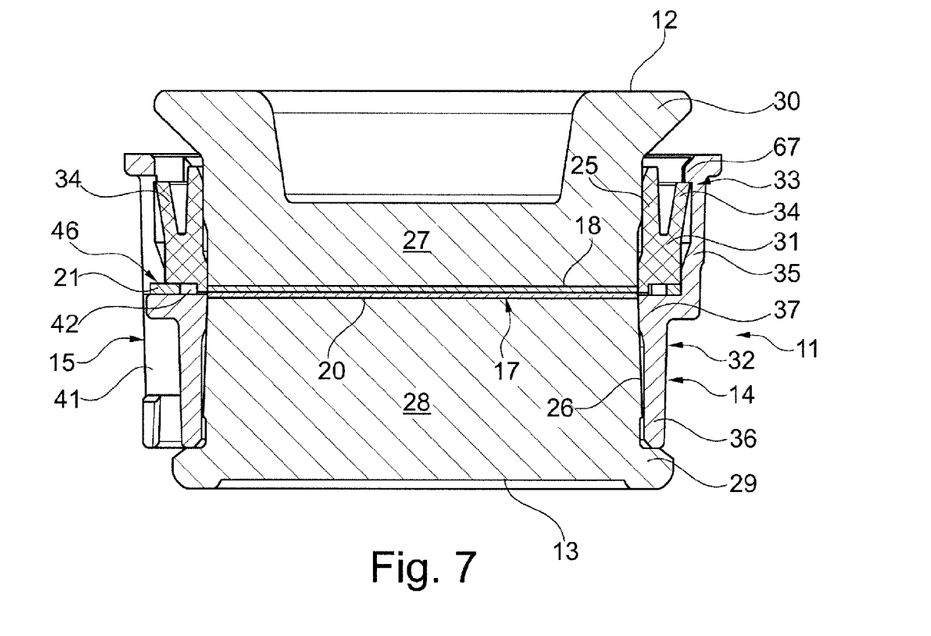
FIG. 7 is a cross-sectional view of an inner cell for an electrochemical test cell.
Figure 8:
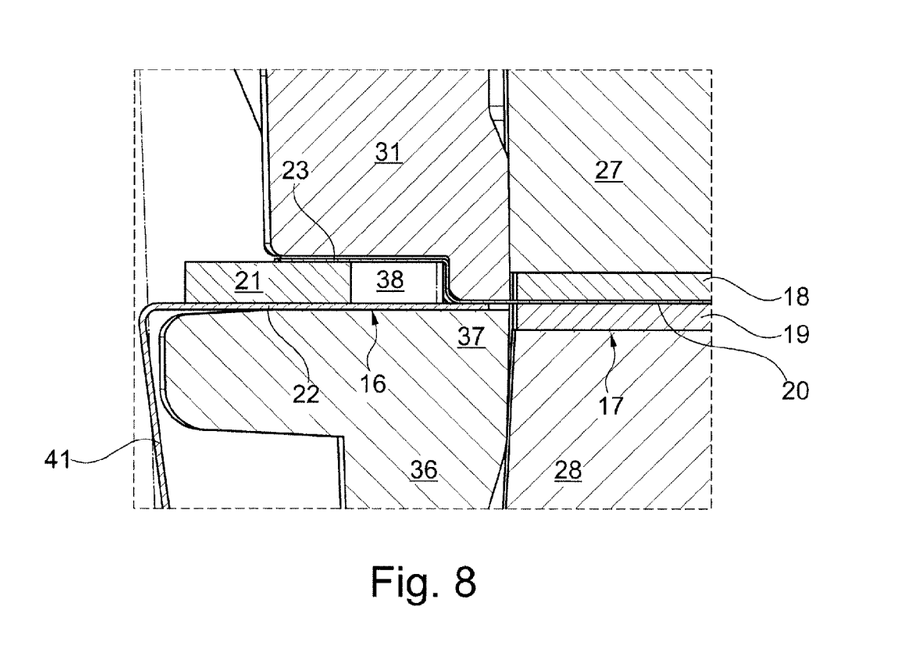
FIG. 8 is an enlarged detail of the dashed region from FIG. 7.

The internal construction of an electrochemical test cell 10 (see FIGS. 6 and 9 to 11), which may also be referred to as an inner cell 11, can be seen from FIGS. 1, 7 and 8. The inner cell 11 comprises a first accumulator 12 consisting of a battery-grade metal, a second accumulator 13 consisting of a battery-grade metal, a reference electrode insert 14, and an electrode arrangement 17 having a working electrode 18, a counter electrode 19 and an electrolyte-impregnated separator 20 separating the working electrode 18 from the counter electrode 19; see FIG. 8. The reference electrode insert 14 comprises a sleeve 15, which is tubular overall, and a reference electrode arrangement 16, which can also be seen best in FIG. 8.

The reference electrode arrangement 16 comprises a support ring 21, a contact ring 22, and an annular, electrolyte-impregnated membrane 23, which will be described in greater detail below. In the present embodiment, the annular membrane 23 and the separator 20 are formed by a uniform membrane element 24; see FIG. 3. The membrane element 24 may for example be a thin, porous plastics film, in particular a porous polyolefin film. Other embodiments are possible and are described below.

Figure 3:
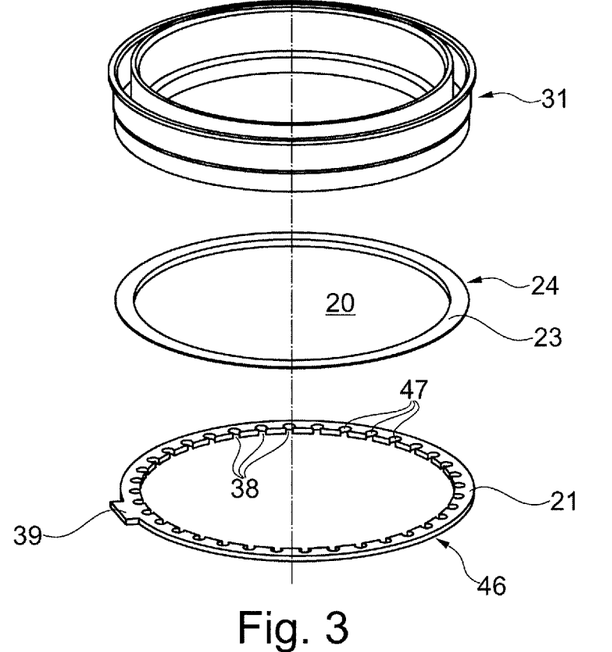
FIG. 3 is an exploded view of a part of the reference electrode insert according to FIG. 2.
Figure 4:
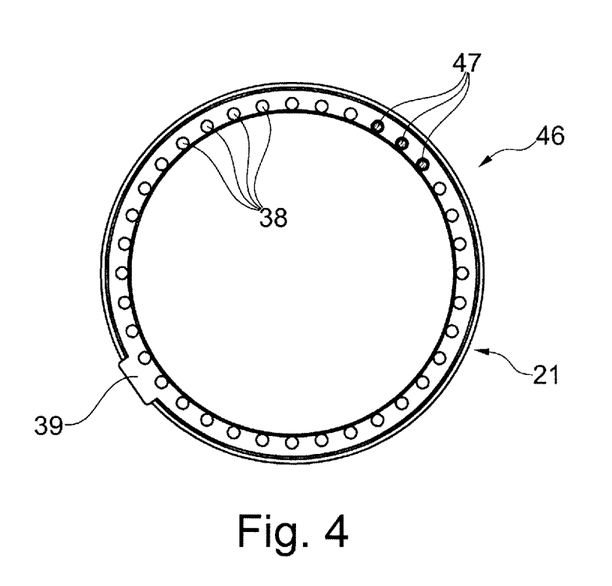
FIG. 4 is a plan view of a support ring for a reference electrode insert.

The support ring 21 serves to receive the reference material 47, for example lithium metal, and comprises for this purpose a plurality of pockets 38, which are preferably distributed uniformly over the circumference of the support ring 21. In FIGS. 3 and 4, merely by way of example, the filling of the pockets 38 with the reference material 47 is shown for three pockets 38 in each case. The pockets 38 are preferably axis-parallel through-holes through the support ring 21, and may be radially inwardly open. The support ring 21 may comprise a positioning means 39, for example a radial projection, by means of which the orientation of the support ring relative to the sleeve 15 may be fixable. The support ring 21 filled with the reference material 47 forms an annular reference electrode 46.

The metal contact ring 22, which is in electrical contact with the support ring 21, has two functions. On the one hand, the contact ring 22 serves to establish the electrical contact of the reference material 47 with an external electrical reference terminal 40 of the test cell 10 (see FIGS. 10 and 11), and can be formed in a manner adapted to this function. For example, the contact ring 22 may be thinner than the support ring 21. The contact ring 22 may advantageously have an angled tab 41 as a spring contact tongue for electrical connection to an external electrical terminal 40. On the other hand, the contact ring 22 advantageously reduces the impedance of the reference electrode 46 (shunt effect at high measurement frequencies).

The electrode arrangement 17 is arranged in the sleeve 15 in the central axial region and is oriented approximately perpendicularly to the central axis of the sleeve 15. The electrode arrangement 17 thus divides the tubular sleeve 15 into a first tube portion 25 for receiving the first accumulator 12 and a second tube portion 26 for receiving the second accumulator 13. The accumulators 12, 13 each have a cylindrical plunger 27, 28, the external diameter of which corresponds to the internal diameter of the corresponding tube portion 25, 26, and so the plungers 27, 28 can be inserted so as to fit into the corresponding tube portion 25, 26. At least one of the accumulators 13 comprises a collar 29, which is designed to stop against the sleeve 15 in a precise fit, at the outer end thereof. This will be described in greater detail below. The other accumulator 12 may likewise comprise a collar 30, for example for improved handleability, at the outer end thereof.

The sleeve 15 advantageously consists of a plurality of, in this case, two sleeve parts 31, 32, which are interconnected captively and firmly by means of a connection means, in this case a snap-in or clip connection means 33. The first sleeve part 31 is annular (see FIG. 3), and comprises a peripheral outer spring tongue 34 and an annular recess 42 for receiving the support ring 21 by clamping. The second sleeve part 32 comprises a first sleeve portion 35 having a larger internal diameter, a second sleeve portion 36 having a smaller internal diameter, and a socket 37 connecting the two sleeve portions 35, 36. On the internal circumference of the first sleeve portion 35, a plurality of for example five latching projections 67, distributed over the circumference, are provided. The first sleeve part 31 can be inserted into the first cylindrical portion 35 of the second sleeve part 32 until the spring tongue 34 latches in behind the latching projections 67, causing the first sleeve part 31 to be firmly and captively connected to the second sleeve part 32 and secured therein. Thus, the first sleeve part 31 forms the first tube portion 25; the second sleeve portion 36 of the second sleeve part 32 forms the second tube portion 26. The second sleeve part 32 comprises a through-opening 61 (see FIG. 1), through which the tab 41 of the contact ring 22 can be passed so as to make possible a simple connection of the contact ring 22 to the external reference terminal 40 through the sleeve 15. The clip connection means 33 may be interconnected so as to be unreleasable, in other words releasable only by destroying the sleeve 15, so as to prevent the user from opening the reference electrode insert 14. However, this does not exclude the possibility of the clip connection means 33 alternatively being releasably interconnectable, for example by means of a tool. Different embodiments of the clip connection means 33 are possible. For example, more than one spring tongue 34 and/or only one latching projection 67 may be provided. Alternatively, the latching projection(s) 67 may be provided on the first sleeve part 31 and the spring tongue(s) 34 may be provided on the second sleeve part 32.

Figure 5:
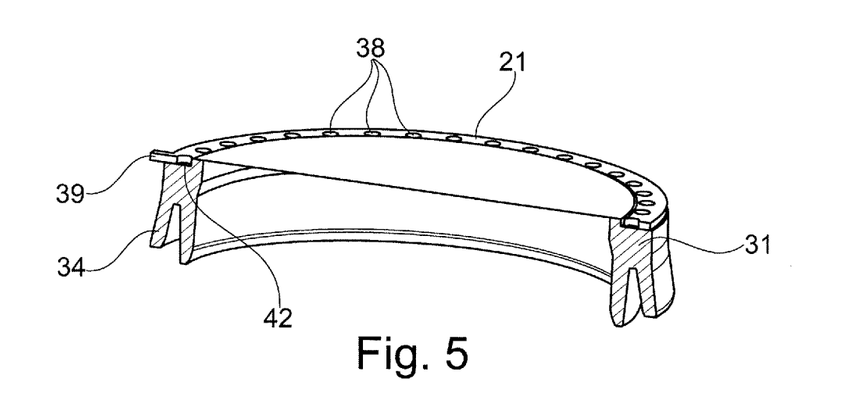
FIG. 5 is a perspective cross-sectional view of a sleeve part having a clamped separator film.
Figure 6:
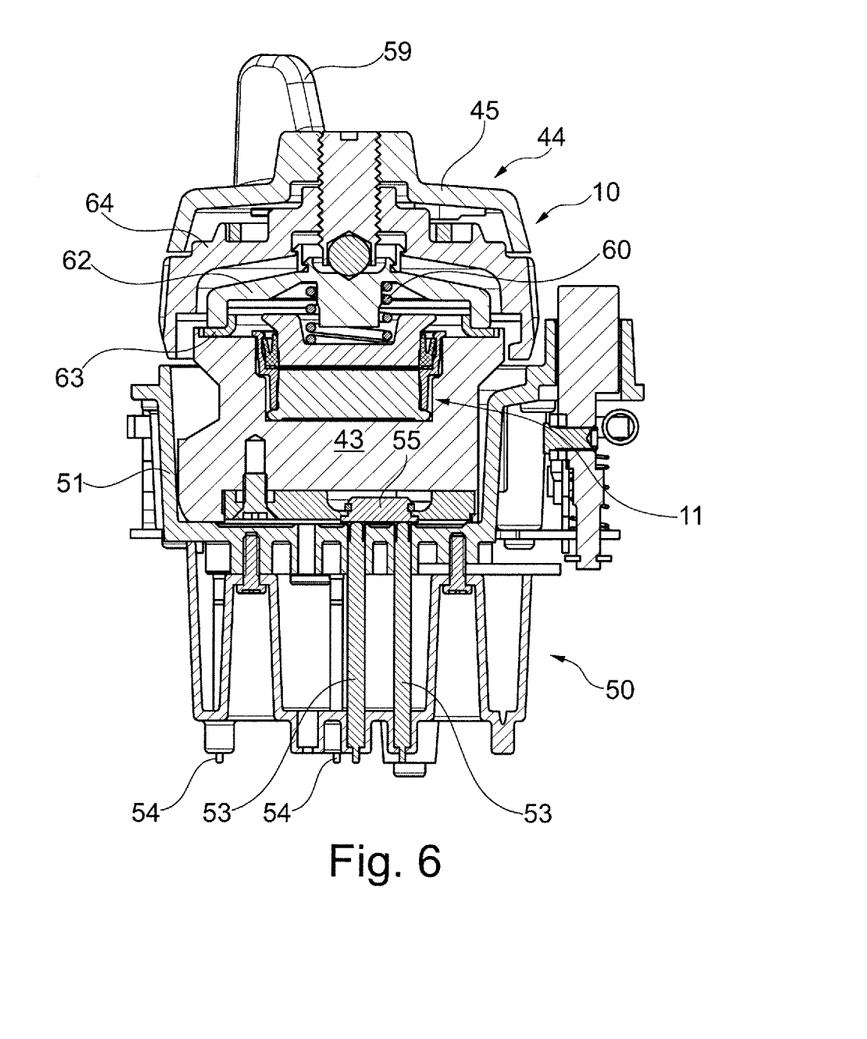
FIG. 6 is a cross-sectional view of an electrochemical test cell.

To assemble a reference electrode insert 14 according to the invention, the manufacturer initially lays the membrane element 24 on the first sleeve part 31, and then presses the support ring 21 into the receptacle 42 of the first sleeve part 31 and clamps it therein, causing the membrane element 24 to be clamped onto the first sleeve part 31 in the manner of a drum skin. This state is shown in FIG. 5. Subsequently, the manufacturer presses a small amount of the reference material, in this case lithium metal, into the pockets 38 of the support ring 21.

Alternatively, the support ring 21 may be coated with the reference material 47 in a planar manner, for example by screen printing, electroplating, vapour deposition, sputtering, chemical vapour deposition CVD, etc. The pockets 38 in the support ring 21 are advantageously unnecessary in this embodiment.

Subsequently, the contact ring 22 is laid in the first sleeve portion 35 of the second sleeve part 32, the tab 41 of the contact ring 22 being passed through the through-opening 61. The first sleeve part 31 is then inserted into the first sleeve portion 35 of the second sleeve part 32 until the snap-in connection means 34, 67 latch in. In this state, the reference material 47 is captively encapsulated in the sleeve 15; see in particular FIG. 8. The dimensions are selected in such a way that the first sleeve part 31 presses the reference electrode arrangement 16, in other words the membrane 23 or the membrane element 24, the support ring 21 and the contact ring 22, against the second sleeve part 32 and the reference electrode arrangement 16 is thus positioned firmly in the sleeve 15. The reference electrode insert 14 formed by the manufacturer in this manner is shown in the centre of the FIG. 1. The reference electrode insert 14 is packaged by the manufacturer in a protective gas, and can be supplied to the user in this form.

An example assembly sequence for the complete test cell 10 is described in the following.

The user initially removes the reference electrode insert 14 from the packaging. The user subsequently places the counter electrode 19, with the active layer facing the separator 20, in the second sleeve portion 36 of the second sleeve part 32 in contact with the separator 20, and inserts the second accumulator 13 into the tube portion 26 of the second sleeve part 32 until the collar 29 stops against the second sleeve part 32. The dimensions are selected in such a way that the plunger 28 of the second accumulator 13 holds the counter electrode 19 in planar contact with the separator 20.

The unit 13, 14, 19 is then rotated through 180°. Subsequently, the user drips a particular amount of electrolyte onto the separator 20. The electrolyte is distributed over the entire membrane element 24, including the annular membrane 23, which thus establishes the electrolyte contact with the reference material arranged in the pockets 38 by means of a "wick effect". The added electrolyte amount has to be at least sufficient to soak the two electrodes, the separator and the annular wick completely.

In the following work step, it is expedient for the unit 13, 14, 19 to rest on an underlay, advantageously in the socket 43, and to be braced against the underlay so as to prevent damage to or perforation of the membrane 23 when the working electrode 18 is laid in and when the first accumulator 12 is inserted.

The unit 13, 14, 19 is then advantageously inserted into the socket 43 of the cell 10, and the working electrode 18 is laid, with the active layer facing the other side of the separator 20, in the first sleeve part 31 in contact with the electrolyte-impregnated separator 20. Subsequently, the first accumulator 12 is inserted into the tube portion 25 of the first sleeve part 31, until the first accumulator 12 holds the working electrode 18 in planar contact with the electrolyte-impregnated separator 20. This state, in which the inner cell 11 is assembled ready for use, is shown in FIG. 7. The membrane element 24 establishes the electrolytic contact between all three electrodes 18, 19, 46; see FIG. 8.

Various alternative assembly methods are possible. For example, the electrolyte can be applied before the electrodes 18, 19 are laid. It is also possible to assemble the working electrode 18 initially and the counter electrode 19 subsequently. The inner cell 11 may also be inserted into the socket 43 only after complete assembly.

Figures 9, 10, 11, 12:
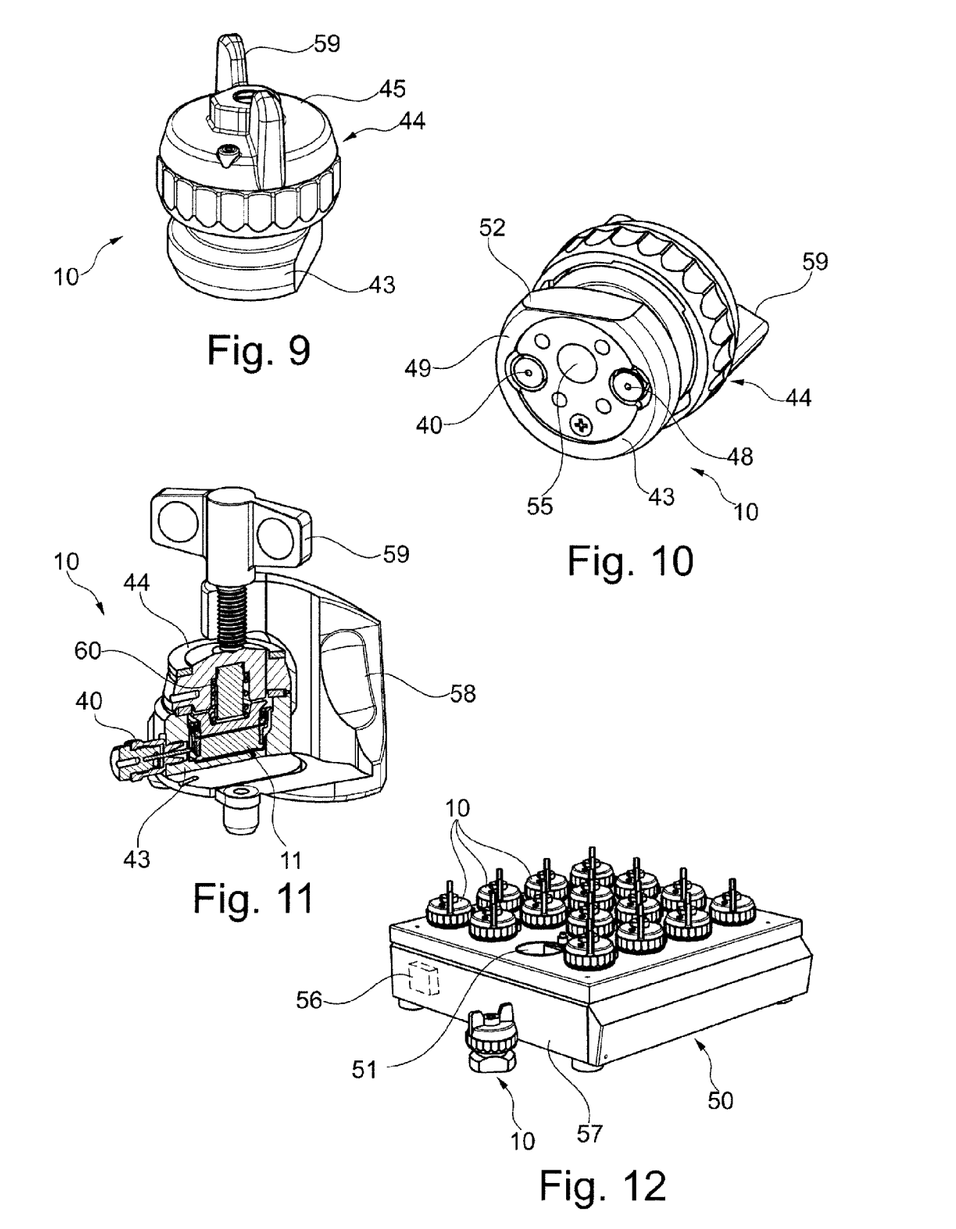
FIG. 9 is a perspective view of an electrochemical test cell.
FIG. 10 is a perspective view of an electrochemical test cell from below.
FIG. 11 is a perspective view of an electrochemical test cell in an alternative embodiment having a screw clamp.
FIG. 12 is a perspective view of a test cell station for receiving a plurality of electrochemical test cells.

The inner cell 11 according to the invention can be used in various applications. One advantageous application is shown in FIGS. 9 and 10. The electrochemical test cell 10 according to FIGS. 9 and 10, referred to as PAT-Cell, comprises a preferably metal, in particular cup-shaped socket 43, for example consisting of high-grade steel, and a cover arrangement 44, which can be connected to the socket 43 via an intermediate cover 64 for example by means of a bayonet fixing and which comprises an inner cover 62. The inner cell 11 is inserted into the socket 43, and the cover arrangement 44 is placed on the socket 43 and connected thereto. The cover arrangement 44 comprises a screw element 45, in this case in the form of a screw cover, which is to be actuated using a handle 59 and by means of which the inner cover 62 is pressed onto the socket 43 while compressing a sealing ring 63, for example made of PE, provided between the inner cover 62 and the socket 43. The socket 43, the inner cover 62 and the seal 63 thus form an inner housing which is sealed in an airtight manner and by means of which the inner cell 11 is hermetically outwardly sealed. The functional separation of the cover arrangement 44 into a connection part 64, for connecting the cover arrangement 44 to the socket 43, and a screw element 45 makes it possible to generate a force of a few thousand N, required for sealing off the inner housing, manually by means of the screw element. This would not be achievable using a single-piece twist cover which takes on both of the above functions.

By means of a spring 60 (see FIG. 6) arranged between the inner cover 62 and the inner cell 11, a defined force of a few N is applied to the inner cell 11 and thus to the electrode arrangement 17. By means of the external terminals, specifically the reference terminal 40, the contact terminal 48 for the working electrode 18 and the contact terminal 49 for the counter electrode 19 via the socket 43 (or in reverse), charge or discharge curves for the electrochemical cell 10 can be recorded and impedance measurements can be taken.

One aspect of the invention provides a test cell station 50 (see FIG. 12) which comprises a plurality of in this case sixteen receptacles 51, each for an electrochemical test cell 10. The receptacles 51 are advantageously arranged in an upper face of the housing 57 and may for example consist of plastics material. A test cell receptacle 51 is shown in cross section in FIG. 6. The test cell 10 can be inserted into the receptacle 51 in a defined orientation, which can be achieved for example by means of a corresponding profile of the socket 43 having a planar lateral surface 52 or by means of other orientation means. In the inserted state, a cell can be fixed in the corresponding receptacle 51 by means of a locking mechanism (not shown). Below the receptacle 51, double-action spring contact pins 54, 53 are provided, which, when a cell 10 is inserted into the receptacle 51, lie against the external contact terminals 40, 48, 49, 55 of the cell 10 under resilient bias, on the one hand, and lie against contacts of a circuit board provided in the station 50 under resilient bias, on the other hand. Preferably, a metal contact element 55, for example a contact button consisting of high-grade steel, is provided on the underside of the test cell 10, which short-circuits two double-action spring contact pins 53 when a cell 10 is inserted into the receptacle 51. In this way, the presence of a test cell 10 in a receptacle 51 can be detected in a simple manner. By means of the double-action spring contact pins 53, 54, interfering and sensitive cable connections can be avoided. A data logger 56 for recording the measurement data, which is shown merely schematically in FIG. 12, is advantageously integrated in the test cell station 50. The contact terminals 40, 48, 55 inserted into the base of the test cell 10 need not necessarily be round, but may also take on other geometric shapes.

Another use of the internal cell 11 according to the invention is shown in FIG. 11. In this case, the internal cell 11 is arranged in a housing known per se of an electrochemical test cell 10. For this cell 10, a screw clamp 58 is provided to generate the sealing force.

In an alternative embodiment of the test cell 10 according to FIGS. 1 to 10, the annular membrane 23 and the disc-shaped separator 20 are two separate elements, the annular membrane 23 being preassembled in the reference electrode insert 14 by the manufacturer, and the separator 20 only being inserted by the user. In this embodiment, the user can insert any desired separator 20. This may for example be advantageous if the user wishes to use a thicker separator 20, for example consisting of a glass fibre mat.

The invention claimed is:

1. A reference electrode insert for an electrochemical test cell, comprising:
   a reference electrode; and
   a sleeve,
   wherein the sleeve is configured to hold the reference electrode, such that when the sleeve holds the reference electrode, the sleeve and the reference electrode form a structural unit with the reference electrode secured in the sleeve,
   wherein the sleeve comprises:
      a first sleeve part; and
      a second sleeve part,
      wherein the first sleeve part and the second sleeve part are configured to interconnect, such that when the first sleeve part and the second sleeve part are interconnected, the first sleeve part and the second sleeve part are securely held together, and
      wherein the first sleeve part has an annular shape,
   wherein the reference electrode comprises:
      a support ring,
      wherein the support ring has at least one recess configured to receive a reference material, and
      wherein the support ring is a metal support ring,
   wherein a membrane element is clamped onto the sleeve via the support ring, and
   wherein the sleeve comprises:
      a first tube portion,
         wherein the First tube portion is configured such that a first accumulator can be inserted into the first tube portion at a first end of the sleeve; and
      a second tube portion,
         wherein the second tube portion is configured such that a second accumulator can be inserted into the second tube portion at a second end of the sleeve.

2. The reference electrode insert according to claim 1, wherein the first sleeve part and the second sleeve part are configured to interconnect via a snap-in connection or via a clip connection.

3. The reference electrode insert according to claim 1, wherein the second sleeve part comprises:
   a first sleeve portion having a first internal diameter;
   a second sleeve portion having a second internal diameter,
   wherein the second internal diameter is smaller than the first internal diameter; and
   a socket connecting the first sleeve portion and the second sleeve portion.

4. The reference electrode insert according to claim 1, wherein the sleeve consists of a thermoplastic, battery-grade plastic material.

5. The reference electrode insert according to claim 4, wherein the sleeve consists of polypropylene or high-density polyethylene.

6. The reference electrode insert according to claim 1, wherein the at least one recess comprises a plurality of recesses distributed over a circumference of the support ring.

7. The reference electrode insert according to claim 1,
wherein the reference electrode insert comprises a contact ring which is in electrical contact with the support ring.

8. An electrochemical test cell incorporating a reference electrode insert according to claim 1, comprising:
a first accumulator;
a second accumulator; and
an electrode arrangement,
wherein the electrode arrangement is arranged between the first accumulator and the second accumulator,
wherein electrode arrangement comprises:
a working electrode;
a counter electrode; and
the reference electrode insert according to claim 1.

9. The electrochemical test cell according to claim 8, further comprising:
a contact face,
wherein the electrochemical test cell is configured to contact a test cell station such that the contact face contacts the test cell station,
wherein the contact face comprises a conductive contact element for detection of the presence of the electrochemical test cell by the test cell station.

10. A test cell station, comprising:
a housing,
wherein at least one receptacle is provided in the housing,
wherein the at least one receptacle is configured to receive a corresponding at least one electrochemical test cell according to claim 8; and
a data logger,
wherein the data logger is integrated in the housing of the test cell station,
wherein the data logger is configured to record charge characteristic curves with respect to the at least one electrochemical test cell according to claim 8.

11. The test cell station according to claim 10, comprising:
a circuit board,
wherein the circuit board is arranged inside the housing; and
spring contact pins,
wherein the spring contact pins are configured to contact contacts on the electrochemical test cell via corresponding first ends of the spring contact pins such that resilient contact is made between the spring contact pins and the contacts on the electrochemical test cell,
wherein the spring contact pins are configured to contact contacts on the circuit board via corresponding second ends of the spring contact pins such that direct, resilient contact is made between the spring contact pins and the contacts on the circuit board, such that the spring contact pins connect the contacts on the electrochemical test cell to the contacts on the circuit board.

12. The reference electrode insert according to claim 1,
wherein the membrane element is electrolyte-impregnated,
wherein when the at least one recess receives the reference material, and the first sleeve part and the second sleeve part are interconnected, the support ring is in contact with the reference material, the membrane element is in contact with the reference material, and the reference material is prevented from falling out.

13. The reference electrode insert according to claim 12,
wherein the sleeve is configured such that when the first sleeve part and the second sleeve part are interconnected, the first accumulator is inserted into the first tube portion at the first end of the sleeve, and the second accumulator is inserted into the second tube portion at the second end of the sleeve,
a working electrode; and
a counter electrode,
can be positioned between the first accumulator and the second accumulator, with as an electrolyte-impregnated separator positioned between the working electrode and the counter electrode, such that the working electrode is in contact with the electrolyte-impregnated separator and the counter electrode is in contact with the electrolyte-impregnated separator, and electrolytic contact is established between the working electrode, the counter electrode, and the support ring with the reference material received in the at least one recess.

14. The electrochemical test cell according to claim 8,
wherein the membrane element is electrolyte-impregnated,
wherein when the at least one recess receives the reference material, and the first sleeve part and the second sleeve part are interconnected, the support ring is in contact with the reference material, the membrane element is in contact with the reference material, and the reference material is prevented from falling out.

15. The electrochemical test cell according to claim 14,
wherein the sleeve is configured such that when the first sleeve part and the second sleeve part are interconnected, the first accumulator is inserted into the first tube portion at the first end of the sleeve, and the second accumulator is inserted into the second tube portion at the second end of the sleeve,
a working electrode; and
a counter electrode,
can be positioned between the first accumulator and the second accumulator, with an electrolyte-impregnated separator positioned between the working electrode and the counter electrode, such that the working electrode is in contact with the electrolyte-impregnated separator and the counter electrode is in contact with the electrolyte-impregnated separator, and electrolytic contact is established between the working electrode, the counter electrode, and the support ring with the reference material received in the at least one recess.

16. The test cell station according to claim 10,
wherein the membrane element is electrolyte-impregnated,
wherein when the at least one recess receives the reference material, and the first sleeve part and the second sleeve part are interconnected, the support ring is in contact with the reference material, the membrane element is in contact with the reference material, and the reference material is prevented from falling out.

17. The test cell station according to claim 16,
wherein the sleeve is configured such that when the first sleeve part and the second sleeve part are interconnected, the first accumulator is inserted into the first tube portion at the first end of the sleeve, and the second accumulator is inserted into the second tube portion at the second end of the sleeve,
a working electrode; and
a counter electrode,
can be positioned between the first accumulator and the second accumulator, with an electrolyte-impregnated separator positioned between the working electrode and the counter electrode, such that the working electrode is in contact with the electrolyte-impregnated separator and the counter electrode is in contact with the electrolyte-impregnated separator, and electrolytic contact is established between the working electrode, the counter electrode, and the support ring with the reference material received in the at least one recess.

18. The reference electrode insert according to claim 1, wherein the reference electrode comprises the reference material, and
wherein the reference material is received by the at least one recess of the support ring.

19. The electrochemical test cell according to claim 8, wherein the reference electrode comprises the reference material, and
wherein the reference material is received by the at least one recess of the support ring.

20. The test cell station according to claim 10, wherein the reference electrode comprises the reference material, and
wherein the reference material is received by the at least one recess of the support ring.

\* \* \* \* \*